US011235140B2

(12) United States Patent
Siess et al.

(10) Patent No.: US 11,235,140 B2
(45) Date of Patent: Feb. 1, 2022

(54) BLOOD PUMP WITH FLOW CANNULA

(71) Applicant: Abiomed Europe GmbH, Aachen (DE)

(72) Inventors: Thorsten Siess, Aachen (DE); Gerd Spanier, Aachen (DE); Walid Aboulhosn, Aachen (DE)

(73) Assignee: Abiomed Europe GmbH, Aachen (DE)

( * ) Notice: Subject to any disclaimer, the term of this patent is extended or adjusted under 35 U.S.C. 154(b) by 111 days.

(21) Appl. No.: 16/329,252

(22) PCT Filed: Aug. 31, 2017

(86) PCT No.: PCT/EP2017/071890
§ 371 (c)(1),
(2) Date: Feb. 28, 2019

(87) PCT Pub. No.: WO2018/041963
PCT Pub. Date: Mar. 8, 2018

(65) Prior Publication Data
US 2019/0216993 A1    Jul. 18, 2019

(30) Foreign Application Priority Data

Sep. 1, 2016  (EP) .................................... 16186860

(51) Int. Cl.
*A61M 1/36* (2006.01)
*A61M 60/857* (2021.01)
*A61M 60/205* (2021.01)
(52) U.S. Cl.
CPC ........ *A61M 60/857* (2021.01); *A61M 1/3659* (2014.02); *A61M 60/205* (2021.01); *A61M 2205/04* (2013.01); *A61M 2210/125* (2013.01)

(58) Field of Classification Search
CPC .. A61M 1/1008; A61M 1/3659; A61M 1/101; A61M 2205/04; A61M 2210/125; A61M 60/857; A61M 60/205
See application file for complete search history.

(56) References Cited

U.S. PATENT DOCUMENTS 6,186,999 B1    2/2001  Chen
6,790,171 B1 *  9/2004  Grundeman ...... A61M 25/0023
                                                600/18

(Continued)

OTHER PUBLICATIONS

International Search Report and Written Opinion for International Application No. PCT/EP2017/071890 dated Dec. 20, 2017 (13 pages).

*Primary Examiner* — Ankit D Tejani
*Assistant Examiner* — Joshua Brendon Solomon
(74) *Attorney, Agent, or Firm* — Botos Churchill IP Law LLP

(57) ABSTRACT

A blood pump for supporting a patient's heart includes a flow cannula having a distal portion including a distal end and a proximal portion including a proximal end opposite the distal end, the distal end of the flow cannula configured to be connected to the patient's heart or a blood vessel to establish fluid communication between the blood pump and the patient's heart and blood vessel, respectively. The flow cannula further includes an intermediate portion attached to the distal portion and the proximal portion, wherein the intermediate portion allows twisting thereof with a lower force than the distal portion and the proximal portion. The intermediate portion can be fully occluded by twisting it. At least a portion of the intermediate portion either alone or in combination with the distal portion is adapted to be permanently attached to the patient's heart or a blood vessel.

24 Claims, 7 Drawing Sheets

(56) References Cited

U.S. PATENT DOCUMENTS

| | | | |
|---|---|---|---|
| 7,022,135 B2 * | 4/2006 | Zilla | A61L 27/34 623/1.39 |
| 2002/0165600 A1 * | 11/2002 | Banas | A61F 2/91 623/1.11 |
| 2003/0153935 A1 * | 8/2003 | Mialhe | A61B 17/12109 606/157 |
| 2004/0059178 A1 | 3/2004 | McCarthy et al. | |
| 2009/0082778 A1 * | 3/2009 | Beane | A61B 17/3468 606/108 |
| 2014/0303427 A1 | 10/2014 | Kerkhoffs et al. | |
| 2016/0121034 A1 * | 5/2016 | Foster | A61M 1/1017 600/16 |
| 2018/0050188 A1 * | 2/2018 | Accisano, III | A61M 39/26 |

\* cited by examiner

BLOOD PUMP WITH FLOW CANNULA

CROSS-REFERENCE TO RELATED APPLICATIONS

This application is a United States National Stage filing under 35 U.S. C. § 371 of International Application No. PCT/EP2017/071890, filed Aug. 31, 2017, which claims the benefit of European Patent Application No. 16186860.9, filed Sep. 1, 2016, the contents of all of which are incorporated by reference herein in their entirety. International Application No. PCT/EP2017/071890 was published under PCT Article 21(2) in English.

BACKGROUND

This invention relates to a flow cannula for a blood pump for supporting a patient's heart. The flow cannula is configured for connecting the blood pump to the patient's heart or a blood vessel. The flow cannula can be separated such that a part connected to the heart or blood vessel remains inside the patient's thorax after removing the blood pump. The invention further relates to a method of removing a blood pump from a patient.

Blood pumps may be inserted into a patient's vessel such as the aorta by means of a catheter, or may be placed in the thoracic cavity or even outside the patient's body. In some applications, and in particular in those cases in which the blood pump is not placed intravascularly, it may be necessary to establish a direct connection to a blood vessel or the heart, e.g. the left ventricle. The flow cannula of the blood pump is inserted into an opening of the heart and secured to the wall of the heart to establish a fluid communication between the blood pump and the patient's heart. An outflow of the blood pump may then be connected to the aorta to pump blood from the left ventricle directly into the aorta.

If the blood pump is no longer needed, e.g. because the heart has recovered, the blood pump is removed. However, complete removal of the flow cannula from the heart would usually require an open thorax surgery and would involve a high risk of severe bleeding, and the opening in the heart would have to be closed. Therefore, the flow cannula is usually separated, e.g. cut, such that the part connected to the heart remains inside the patient's thorax. A clip, clamp or the like is used to close the remaining part of the flow cannula. However, the flow cannula is usually cut close below the patient's skin to facilitate handling if complications occur. Thus, the remaining part of the flow cannula is usually relatively long and the clamp may be bulky. This may affect the surrounding tissue and may cause irritations or even inflammations. Apart from that, there may be a risk that the flow cannula, which may be relatively stiff and may have a relatively large diameter, cannot be clamped tightly such that blood leaks into the patient's thorax.

SUMMARY OF THE INVENTION

It is therefore an object of the present invention to provide a flow cannula for a blood pump, and a blood pump with such a flow cannula, wherein the flow cannula can be easily occluded to stop the blood flow and subsequently separated, both preferably by a minimally invasive procedure, wherein further preferably interference of a part of the flow cannula that remains inside the patient with surrounding tissue can be reduced.

This object is achieved according to the present invention by a flow cannula and a method having the features of the independent claims. Preferred embodiments and further developments of the invention are specified in the claims dependent thereon.

According to the invention, a flow cannula for a blood pump for supporting a patient's heart comprises a distal end and a proximal end opposite the distal end along a longitudinal axis of the flow cannula. The distal end of the flow cannula is configured to be connected to the patient's heart or a blood vessel in order to establish a fluid communication between the blood pump and the patient's heart and blood vessel, respectively. The flow cannula comprises a distal portion having said distal end, a proximal portion having said proximal end. The flow cannula further comprises an intermediate portion attached to at least one of the distal portion and the proximal portion. The intermediate portion allows at least one of clamping and twisting, in particular twisting, thereof with a lower force than at least one of the distal portion and the proximal portion. The intermediate portion is configured to be fully occluded by twisting thereof. Throughout this disclosure, the term "distal" refers to directions away from a user, e.g. a surgeon, and towards the heart, whereas the term "proximal" refers to directions towards a user.

At least a portion of the intermediate portion either alone or in combination with the distal portion is adapted to be permanently attached to the patient's heart or a blood vessel. In other words, said portion of the intermediate portion either alone or in combination with the distal portion is adapted to remain inside the patient's body after removal of the blood pump. Vice versa, preferably at least the proximal portion, possibly the proximal portion and the distal portion, in combination with the remaining part of the intermediate portion is adapted to be removed from the patient's body. Since only a small part of the flow cannula is left behind in the patient, fewer irritations and inflammations occur.

The flow cannula, which is designed in multiple portions, in particular a proximal portion, a distal portion and an intermediate portion allows for improved separation of the flow cannula during removal of the blood pump, wherein the portion that will remain in the patient's body causes less interference with surrounding tissue. The flow cannula can be easily occluded in a minimally invasive surgery by twisting the intermediate portion. In particular, the intermediate portion is configured to be twisted such it is fully occluded and a blood flow through the flow cannula is stopped. Twisting of the intermediate portion can be caused by twisting the proximal portion relative to the distal portions because twisting of the intermediate portion requires less force than twisting of at least the distal portion, preferably both of the distal and proximal portions.

Since the intermediate portion requires less force for twisting or clamping or both clamping and twisting, it can be easily and securely occluded. A smaller clamp or clip compared to a clamp or clip that would be necessary to occlude the distal portion is sufficient to occlude the intermediate portion of the flow cannula. Twisting of the intermediate portion allows for provisional occlusion of the flow cannula which may then be finally closed by a clamp or clip or other suitable means, such as a cable, wire or the like. Since lower forces are required to manipulate the intermediate portion, the procedure of occluding the flow cannula and removing the proximal portion can be done minimally invasive, which bears less risk for the patient. Moreover, alternatively or in addition to twisting the intermediate portion, a loop or cutting wire can be used that is looped around the intermediate portion to clamp it by pulling tight the loop or cutting wire. The term "clip" or "clamp" refers to a piece that is placed around the flow cannula, in particular the twisted portion of the intermediate portion, to securely and finally close it such that the flow cannula can be cut or otherwise separated. The clip or clamp can be applied in a minimally invasive procedure. In contrast to that, known cannulas may require bulky instruments, like a scissor-like surgical clamp, to stop the blood flow. This can be done only in an open thorax surgery.

The distal and proximal portions of the flow cannula may be releasably connected to each other, e.g. by a releasable connector, such as a male/female connector, threads, bayonet mount, quick coupling, magnets or the like. Alternatively, the distal and proximal portions of the flow cannula may be connected via a predetermined breaking line, e.g. a circumferential notch. Thus, the proximal and distal portions can be separated by a low force while the intermediate portion remains attached to both the proximal portion and the distal portion.

Although releasably connected, however, inadvertent separation of the proximal and distal portions should be avoided. Therefore, in case a predetermined breaking line is provided, the predetermined breaking line should have a minimum resistance to withstand low breaking forces. In particular, it may be advantageous to design the predetermined breaking line such that an instrument, such as a hemostat or other clamp or cutting tool, is necessary to separate the proximal and distal portions. It may also be possible to protect the predetermined breaking line, e.g. by a cover, or a tear strip or the like may be provided. One or more, such as two, three, four, five or six, security filaments may be provided attached to the proximal and distal portion, respectively, in order to keep the proximal and distal portions together. The security filaments may be arranged outside the intermediate portion, e.g. evenly spaced about the circumference of the flow cannula. They may be cut or otherwise separated in order to allow separating the proximal and distal portions from each other.

When separated from each other, the proximal and distal portions may be axially movable with respect to each other, which may be achieved by axially compressing or stretching the intermediate portion or by twisting the intermediate portion, which causes the proximal and distal portions to get closer to each other. Alternatively, the distal and proximal portions may be integrally formed and intended not to be separated. For example, the distal and proximal portions may form a single tubular member, wherein the intermediate portion is placed over the tubular member like a jacket.

More specifically, the intermediate portion of the flow cannula may have a distal end and a proximal end, the distal end of the intermediate portion being attached to the distal portion of the flow cannula and the proximal end of the intermediate portion being attached to the proximal portion of the flow cannula. Consequently, while the flow cannula is being prepared for complete separation no blood leaks from the flow cannula because the intermediate portion bridges the gap between the proximal and distal portions even when the proximal and distal portions have been separated. It will thus be appreciated that the intermediate portion is preferably attached to at least the distal portion, preferably both the proximal and distal portions, in a fluid tight manner in order to conduct a blood flow between the distal portion and the proximal portion. For example, it may be glued, welded, clamped, bonded or otherwise attached. In embodiments, in which not both ends of the intermediate portion are attached, i.e. fixedly secured, to the proximal portion and distal portion, respectively, the respective free end may be at least disposed on or about the respective end portion.

In an embodiment the intermediate portion is attached to the distal and proximal portions of the flow cannula such that it at least partially overlaps at least one of, preferably each of, the distal and proximal portions of the flow cannula. That means that during operation of the blood pump, when the proximal and distal portions of the flow cannula are connected to each other, the intermediate portion does not have contact with the blood flowing through the flow cannula if it completely overlaps the proximal and distal portions. Thus, the intermediate portion can be made of a variety of materials that would not be suitable for long term blood exposure. Further, the intermediate portion can be made of a very thin material, which could bear the risk of tearing if it had to conduct the blood flow during the entire operation of the blood pump. Only during separation of the flow cannula, the intermediate portion will have direct contact with the blood flow as described in more detail below. Thus, in particular but not exclusively in this embodiment, the intermediate portion may have a wall thickness of less than about 150 μm, preferably about 30 μm, and may comprise a tubular polymer film, such as polyethylene terephthalate (e.g. Dacron®), polyurethane or ePTFE. For instance, the wall thickness may range from about 5 μm to about 100 μm for polyurethane and from about 300 μm to about 1,000 μm for ePTFE. The thin polymer film is particularly suitable for twisting and thereby fully occluding the flow cannula as described above.

The intermediate portion may be gathered, in particular axially gathered, when the distal and the proximal portions of the flow cannula are connected to each other. The intermediate portion may behave in a bellows-like manner, i.e. it may fold in a zig-zag manner, or it may simply be compressed in an axial direction. If the intermediate portion is gathered or compressed when the proximal and distal portions are connected, the intermediate portion can unfold or decompress when the proximal and distal portions are moved away from each other without stretching it. In other words, there is no tension on the intermediate portion when the proximal and distal portions are spaced apart. This allows for easy clamping and if necessary twisting of the intermediate portion without having to hold a tension on the intermediate portion, which is advantageous for a minimally invasive procedure. However, in any embodiment, the intermediate portion may be stretchable in a direction of the longitudinal axis.

Apart from that, in any embodiment the intermediate portion is sized and dimensioned not to interfere with an axial movement of the proximal and distal portions, i.e. the intermediate portion is not too tight about the proximal and distal portions. For instance, a slight gap may be provided between the intermediate portion and at least one of, preferably both of, the proximal and distal portions. Since the intermediate portion may be attached to the proximal and distal portions, the intermediate portion may be slightly tapered, i.e. have a slightly larger diameter in the middle compared to its ends.

In another embodiment, in particular where the distal and proximal portions are integrally formed, the intermediate portion may comprise an attachment member, such as a disc at its distal end, which is configured to be attached to the patient's heart, e.g. by suturing, in particular permanently. Preferably, the proximal end of the intermediate portion is attached to the proximal portion. In this embodiment, the proximal and distal portions of the flow cannula will not be separated but pulled out of the heart as a single piece. By pulling the proximal and distal portions, the intermediate portion will be stretched or unfolded as described above such that it can be twisted and clamped. The intermediate portion will be cut, such that only the attachment member along with a part of the intermediate portion is left behind in the patient to close the opening in the patient's heart. The proximal and distal portions are completely removed. In order to avoid inadvertent retraction of the proximal and distal portions, security filaments similar to those mentioned above can be provided, which are secured to the attachment member and the proximal portion.

The attachment member is preferably made of a material that allows suturing of the attachment member to the tissue of the heart, such as a felt or the like. In one embodiment the attachment member may comprise radially extending sections, such as three, four, five or six, with gaps between the sections. Upon twisting the intermediate portion, the sections will get closer to each other in a circumferential direction, such that the underlying heart tissue will be twisted and compressed in a circumferential direction about the opening to thereby narrow the opening in the heart tissue, in particular when the proximal and distal portions have been retracted from the heart. This reduces the wound size after the flow cannula has been removed. The wound is then closed by means of the compressed attachment member and the part of the intermediate portion that remains inside the patient.

In still another embodiment the intermediate portion may be attached to the distal and proximal portions such that the distal and proximal portions are axially spaced from each other and the intermediate portion is disposed between the distal and proximal portions. In other words, the proximal and distal portions are not directly connected to each other but are connected via the intermediate portion. In this embodiment, the intermediate portion conducts the blood flow during operation of the blood pump between the proximal and distal portions. Thus, in particular in this embodiment, the intermediate portion may comprise a polymer tube, preferably silicone tube or polyurethane tube, which is suitable for long term blood exposure.

In any of the above described embodiments, the intermediate portion is preferably a flexible tubular member. The proximal and distal portions of the flow cannula preferably are tubular members, too. Advantageously, the distal portion of the flow cannula is as short as possible, in either case shorter than the proximal portion of the flow cannula in a longitudinal direction, wherein a length of the distal portion is preferably less than 50%, more preferably less than 25%, most preferably less than 15% of a length of the proximal portion. For example, the distal portion may have a length of 0.5 cm to 3 cm, e.g. 1 cm, and the proximal portion may have a length of 5 cm to 9 cm, e.g. 7 cm. The flow cannula may have a diameter of about 2 to 15 mm, preferably about 6 to 8 mm.

Preferably, the blood pump is sized and configured to be placed in the patient's thoracic cavity. This allows an application in which the blood pump is fully implanted in a patient's body, e.g. connected to the patient's heart and aorta. In other embodiments the blood pump may include a pumping device that is configured to be placed extracorporeal, wherein the flow cannula extends through the patient's skin.

A system may comprise a blood pump as described above and at least one clip or clamp that is sized and configured to be placed around the intermediate portion in order to fully occlude the flow cannula. In particular, the clip or clamp may be sized and shaped to be placed around the intermediate portion when the proximal and distal portions are spaced from each other. After the clip or clamp has been placed around the intermediate portion, the proximal portion of the flow cannula can be removed, e.g. by cutting the intermediate portion as described in more detail below.

An exemplary method of using the blood pump as described above, in particular removing the blood pump from a patient, includes the following steps. If the proximal and distal portions of the flow cannula are connected, e.g. by means of a releasable connector or predetermined breaking line, the proximal and distal portions are separated and axially moved apart from each other. The intermediate portion may then unfold or stretch but remains connected to the proximal and distal portions. The intermediate portion is then occluded in order to occlude the flow cannula and stop the blood flow through the flow cannula. If necessary or indicated by the application, the intermediate portion may first be twisted in order to obtain a provisional occlusion. At the same time, by twisting the intermediate portion its diameter is reduced, which makes it possible to use a small clip. The twisted or untwisted intermediate portion is then clamped by a clamp, clip or the like in order to fully and definitely occlude the flow cannula. The proximal portion of the flow cannula can then be removed, e.g. by cutting the intermediate portion at a location proximal with respect to the clip. The distal portion along with part of the intermediate portion and the clip remains inside the patient. This procedure can be performed minimally invasively. The parts remaining inside the patient are small and not bulky in order to reduce or avoid interference with surrounding tissue. Irritations and inflammations can be reduced or avoided.

In another exemplary embodiment, the proximal and distal portions form a single piece and will not be separated. The intermediate portion has an attachment member at its distal end that is securely attached to the patient's heart, while the proximal end of the intermediate portion is attached to the proximal portion of the flow cannula. Once the flow cannula is to be removed, the single piece comprising the proximal and distal portions is pulled out of the heart, such that the intermediate portions unfolds and/or stretches. It is pulled far enough out of the heart to be able to twist and clamp and subsequently cut the intermediate portion. Only a distal part of the intermediate portion along with the attachment member remains inside the patient. This can further reduce the size of material that is left behind in the patient and improve healing of the punch hole in the heart muscle.

BRIEF DESCRIPTION OF THE DRAWINGS

The foregoing summary, as well as the following detailed description of preferred embodiments, will be better understood when read in conjunction with the appended drawings. For the purpose of illustrating the present disclosure, reference is made to the drawings. The scope of the disclosure is not limited, however, to the specific embodiments disclosed in the drawings. In the drawings.

DETAILED DESCRIPTION

Figure 1:
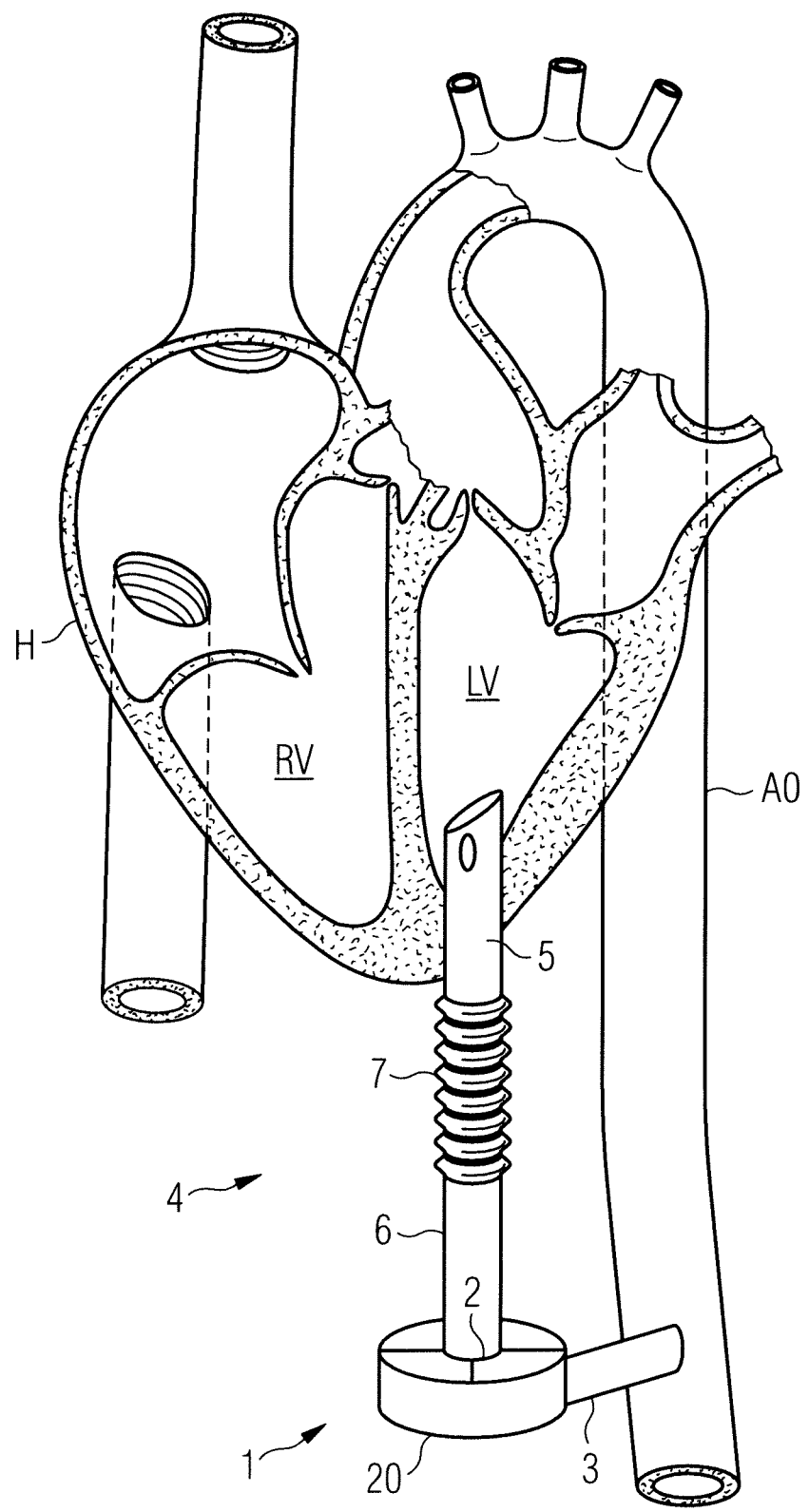
FIG. 1 shows a patient's heart with a blood pump attached thereto.

Referring to FIG. 1 a blood pump 1 is illustrated inserted into a patient's heart H. The blood pump 1 is placed in the thoracic cavity and is directly connected to the left ventricle LV of the heart H by means of a flow cannula 4, which in this application is an inflow cannula because blood is drawn into the flow cannula 4, conveyed into a pump casing 20 through an inlet 2 by means of an impeller (not shown) in the pump casing 20, and further conveyed out of the blood pump 1 through an outflow cannula 3 that is attached to the aorta AO. The flow cannula 4 has a distal portion 5 secured to the wall of the heart H, a proximal portion 6 connected to the inlet 2 of the pump casing 20 and an intermediate portion 7 attached to the distal portion 5 and proximal portion 6 as described in more detail below. The blood pump 1 supports the patient's heart H. Once the blood pump 1 is to be removed, the flow cannula 4 is separated and the remaining distal part of the flow cannula 4 is closed and left behind in the thoracic cavity.

Figure 2A:
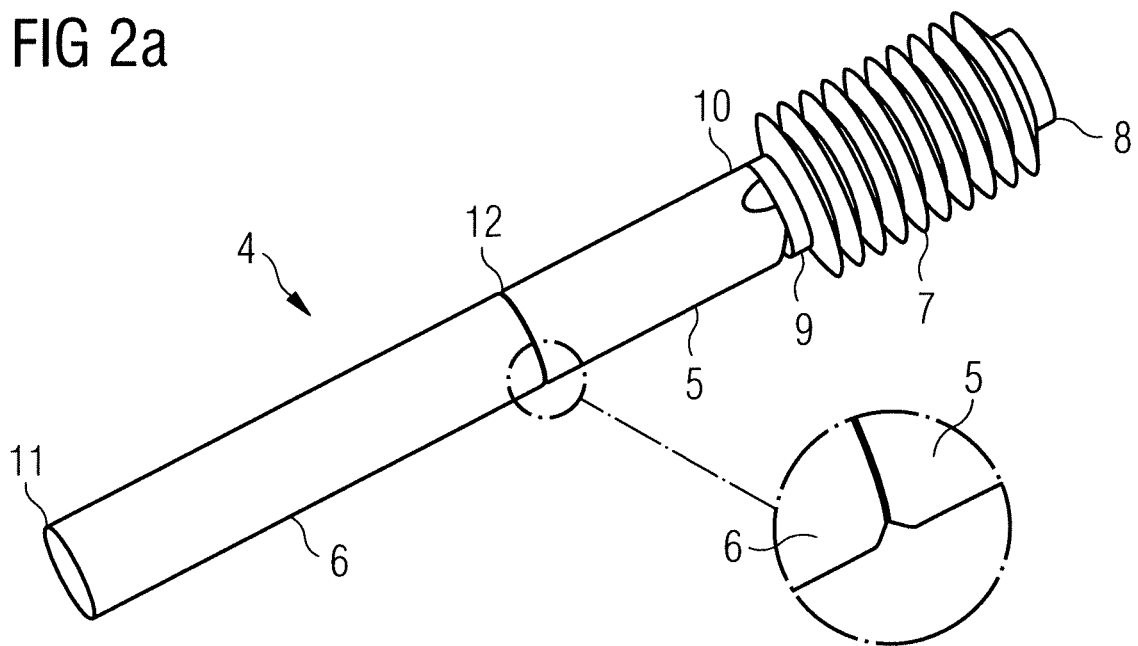
FIGS. 2a and 2b show an embodiment of a flow cannula.
Figure 2B:
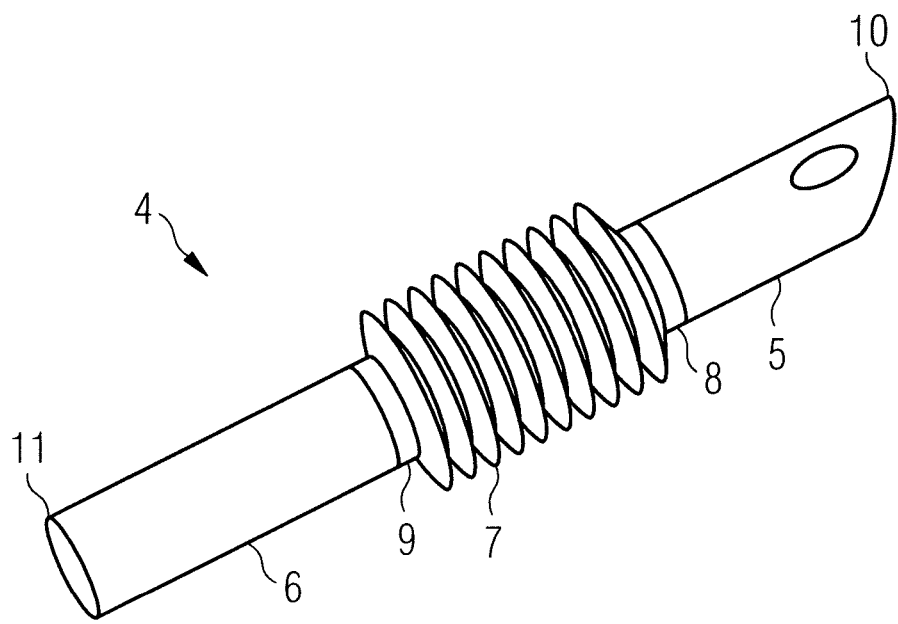

The flow cannula 4 is illustrated in more detail in FIGS. 2a and 2b. FIG. 2a shows an unassembled view in order to illustrate the connection 12 between the proximal and distal portions 5, 6. The proximal and distal portions 5, 6 are releasably connected to each other, e.g. by means of a predetermined breaking line, which may be formed e.g. by a circumferential notch (see enlarged cutout), or by any other releasable connector, such as threads, male/female connector, bayonet mount or the like. The flow cannula 4 has a distal end 10 that is inserted into the patient's heart H as illustrated in FIG. 1 and an opposing proximal end 11 that is attached to the pump casing 20. The distal end 10 may be sloped or tapered to facilitate insertion into the heart H.

The intermediate portion 7 has a distal end 8 that is attached to the distal portion 5 and a proximal end 9 that is attached to the proximal portion 6 as shown in FIG. 2b. Thus, the intermediate portion 7 overlaps both the distal portion 5 and the proximal portion 6. It will be appreciated that the intermediate portion 7 may be attached to the distal and proximal portions 5, 6 such that it overlaps only one of them. The intermediate portion 7 is gathered on the distal and proximal portion 5, 6. Since the distal and proximal portions 5, 6 are connected as shown in FIG. 2a, the intermediate portion 7 does not have contact to the blood flowing through the flow cannula 4 during operation of the blood pump 1.

Figure 3A:
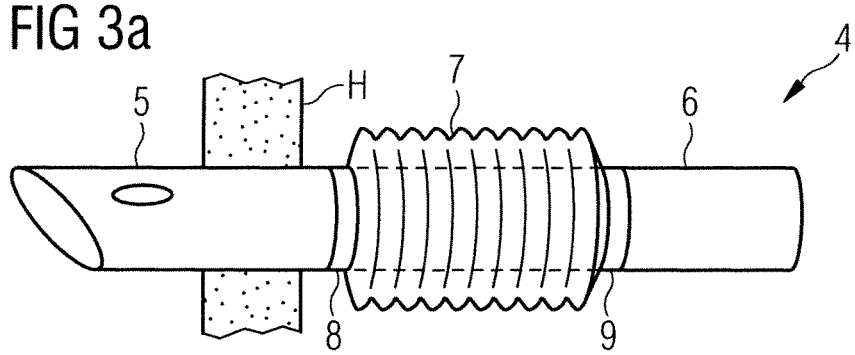
FIGS. 3a to 3e show the flow cannula of FIGS. 2a, 2b during use.
Figure 3B:
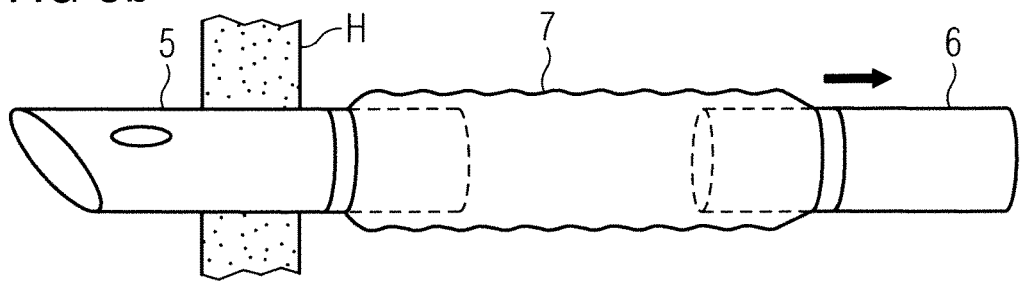

With reference to FIGS. 3a to 3e an exemplary method of removing a flow cannula from a patient's body, e.g. during removal of the blood pump 1 of FIG. 1, including the flow cannula 4 of FIG. 2b, is described. While the blood pump 1 is shown as a centrifugal blood pump, it will be appreciated that the flow cannula 4 can be used in combination with another medical device, in particular another type of blood pump, such as an axial blood pump or a mixed-type (centrifugal/axial) blood pump. FIG. 3a is substantially the same view as FIG. 2b and shows the flow cannula 4 during operation of the blood pump 1. After operation of the blood pump 1 has been stopped, the flow cannula 4 has to be separated to remove the proximal portion 6 from the patient. As illustrated in FIG. 3b, the proximal portion 6 is separated from the distal portion 5 by disconnecting the releasable connector 12, which may be done e.g. by breaking the flow cannula 4 at a predetermined breaking line. Other connection mechanisms, such as a threaded connection may be used but are not shown in FIG. 3b for the sake of simplicity. While the distal portion 5 remains attached to the patient's heart H, the proximal portion 6 is axially moved away from the distal portion 5. The intermediate portion 7 unfolds or stretches and bridges the created gap between the distal and proximal portions 5, 6. Therefore, the intermediate portion 7 is attached to the proximal and distal portions 5, 6 in a fluid tight manner.

Figure 3C:
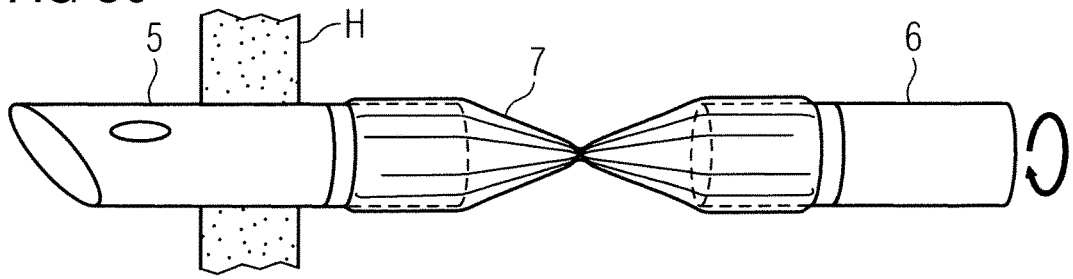
Figure 3D:
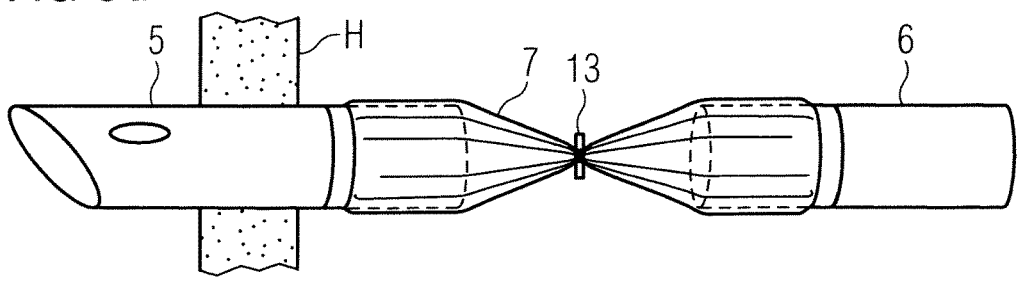
Figure 3E:
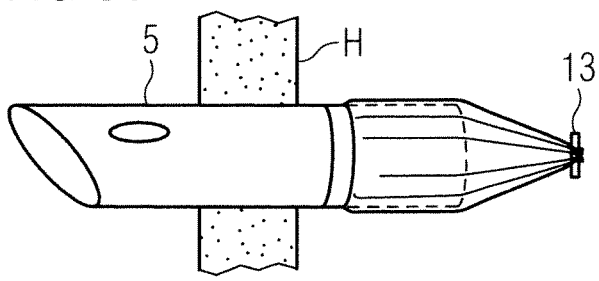

Since the intermediate portion 7 is made of a thin polymer film, it can be easily twisted to provisionally fully occlude the flow cannula 4 as shown in FIG. 3c to stop the blood flow through the flow cannula 4. A clip 13 is then placed around the twisted intermediate portion 7 (FIG. 3d) for final occlusion and the intermediate portion 7 is separated, e.g. by cutting (FIG. 3e). The remaining parts do not require much space in the thoracic cavity and can remain in the thoracic cavity without causing severe irritations or inflammations.

With reference to FIGS. 4a to 4d an exemplary method during removal of a blood pump according to another embodiment is described. In contrast to the embodiment of FIGS. 3a to 3e, the flow cannula 14 comprises an intermediate portion 17 that does not overlap the distal and proximal portions 15, 16 but is disposed between them and connected to the proximal portion 15 with its proximal end 18 and to the distal portion 16 with its distal end 19. Thus, the intermediate portion 17 is in contact with the blood flowing through the flow cannula 14 and is preferably made of a material suitable for long term blood exposure, such as silicone or polyurethane. The intermediate portion 17 is not as thin as the intermediate portion 7 of the previous embodiment, but is softer than the distal and proximal portions 15, 16 to allow clamping and if applicable twisting thereof with a lower force than at least the distal portion 15.

Figure 4A:
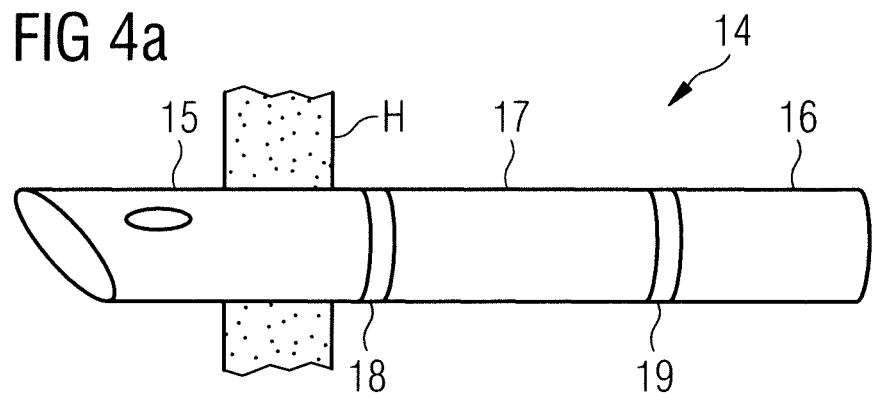
FIGS. 4a to 4d show a flow cannula according to another embodiment during use.
Figure 4B:
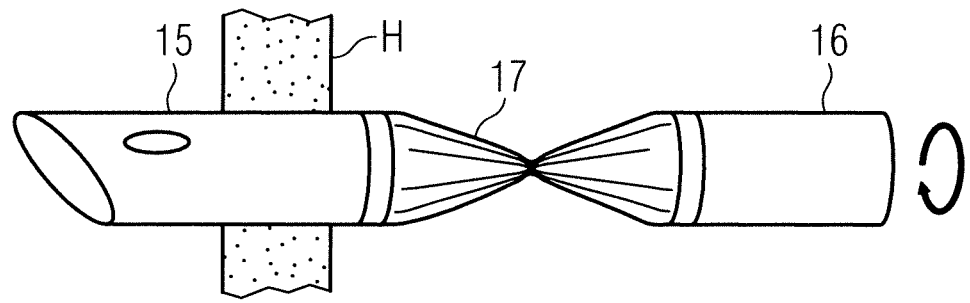
Figure 4C:
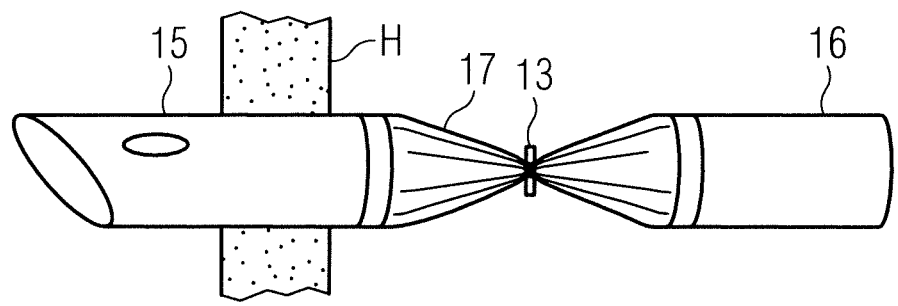
Figure 4D:
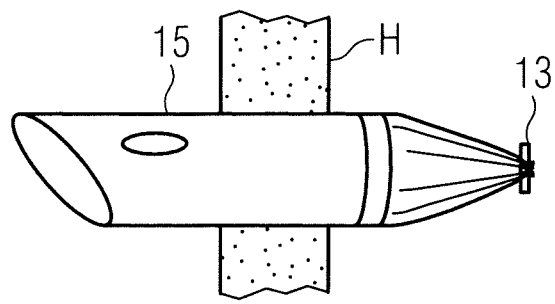

As shown in FIG. 4b, the intermediate portion 17 is twisted to create a provisional full occlusion of the flow cannula 14 to stop the blood flow through the flow cannula 14. It will be appreciated that this step may be omitted and that the clip 13 (FIG. 4c) can be placed over the twisted or untwisted intermediated portion 17 to create a full occlusion of the flow cannula 14. As in the previous embodiment, the intermediate portion 17 is then separated to remove the proximal portion 16 from the patient, while the distal portion 15 remains attached to the patient's heart H (FIG. 4d).

With reference to FIGS. 5a to 5e an exemplary method during removal of a blood pump according to yet another embodiment is described. The flow cannula 24 includes a jacket-like intermediate portion 27 that comprises an attachment member 30, which may be in the form of a disc, plate or sheet, at its distal end 29 opposite the proximal end 28, which is shown in more detail in FIGS. 6 and 7. The attachment member 30 is directly attached to the patient's heart H, e.g. sutured, and is configured to stay attached to the heart H permanently. Except for the attachment member 30, the intermediate portion 27 is substantially similar to the intermediate portion 7 of the embodiment of FIGS. 3a to 3e, e.g. with respect to the material and rigidity characteristics. The flow cannula 24 comprises a tube having a proximal portion 26 and a distal portion 25 that are integrally forming. In contrast to the previous embodiments, the proximal portion 26 and distal portion 25 will not be separated but are formed as a single piece. The intermediate portion 27 is placed over the tube and may be connected to particularly the proximal portion 26 with the proximal end 28. It may be sufficient if the intermediate portion 27 is attached to the proximal portion 26 by friction fit but a secure and fluid tight attachment may be preferred.

Figure 5A:
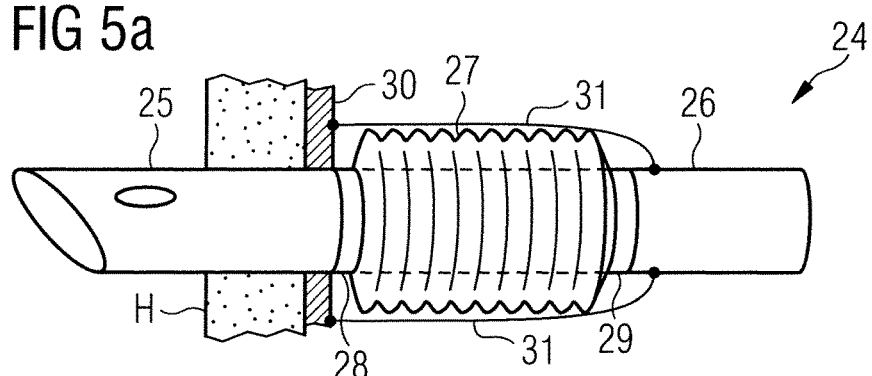
FIGS. 5a to 5e show a flow cannula according to another embodiment during use.
Figure 5B:
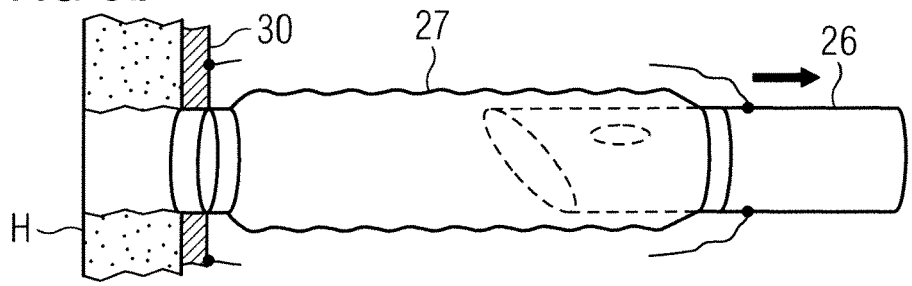
Figure 5C:
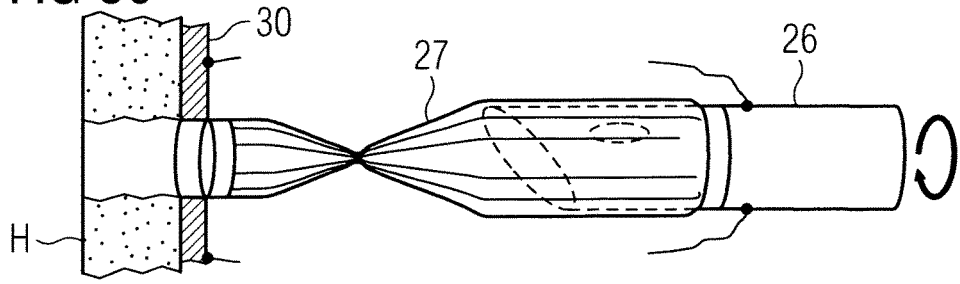

During operation of the blood pump, the attachment member 30, which may be made of a felt material or the like, is fixed to the heart H, e.g. sutured, and the distal portion 25 extends into the heart H (FIG. 5a). When the blood pump is to be removed, the tube including the proximal portion 26 and the distal portion 25 is pulled out of the heart H as shown in FIG. 5b. Since the disc 30 is securely fixed to the heart H and the proximal end 28 of the intermediate portion 27 is attached to the proximal portion 26, the intermediate portion 27 will unfold or stretch as shown in FIG. 5b. It will be appreciated that any fixation between the intermediate portion 27 and the proximal portion 26 would be appropriate that allows for this action, e.g. permanent fixation or sufficiently strong friction fit. It may be possible that the proximal end 28 of the intermediate portion 27 slides along the proximal portion 26.

In order to prevent the tube from being pulled out of the heart accidentally, security filaments 31 are provided that attach to the tube and the attachment member 30 as shown in FIG. 5a. They are cut or otherwise separated in order to be able to retract the tube as shown in FIG. 5b. The part of the security filaments 31 that remains inside the patient's body is kept as short as possible. More than one, such as two, three, four, five or six security filament 31 may be provided.

Figure 5D:
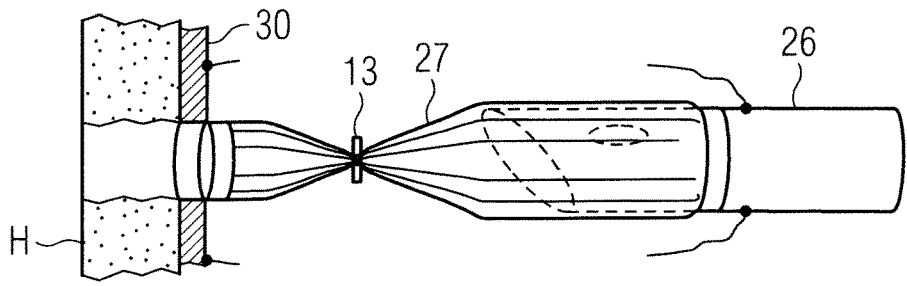
Figure 5E:
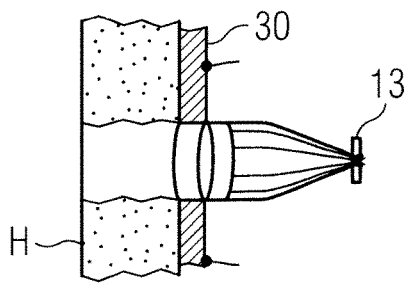

As in the previous embodiments, the intermediate portion 27 is twisted to provisionally close it (FIG. 5c) to stop the blood flow through the flow cannula 24. This is done by twisting the proximal portion 26, which requires sufficient fixation of the intermediate portion 27 on the proximal portion 26. The intermediate portion 27 is then clamped by clip 13 (FIG. 5d). Finally, the intermediate portion 27 is cut, such that the entire tube including the distal portion 25 and the proximal portion 26 along with the cut part of the intermediate portion 27 are removed from the patient. Only the attachment member 30 with a distal part of the intermediate portion 27 remains inside the patient attached to the heart H to close the opening in the heart H. Since only a small part of the flow cannula 24 remains inside the patient, irritations of the surrounding tissue and the risk of inflammations can be reduced.

Figure 6:
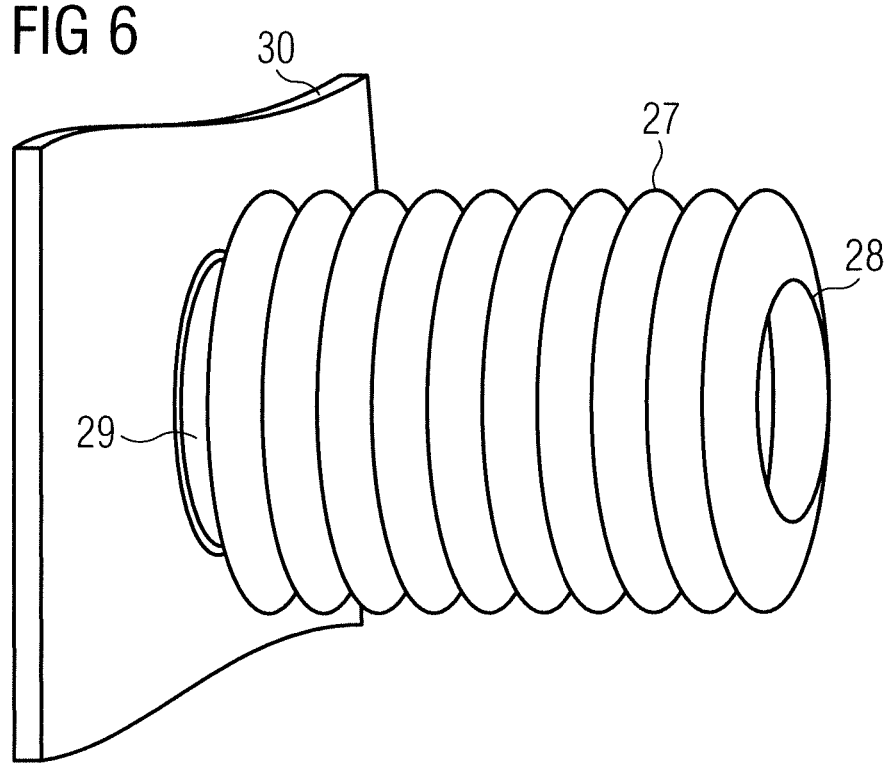
FIG. 6 shows an intermediate portion according to one embodiment.
Figure 7:
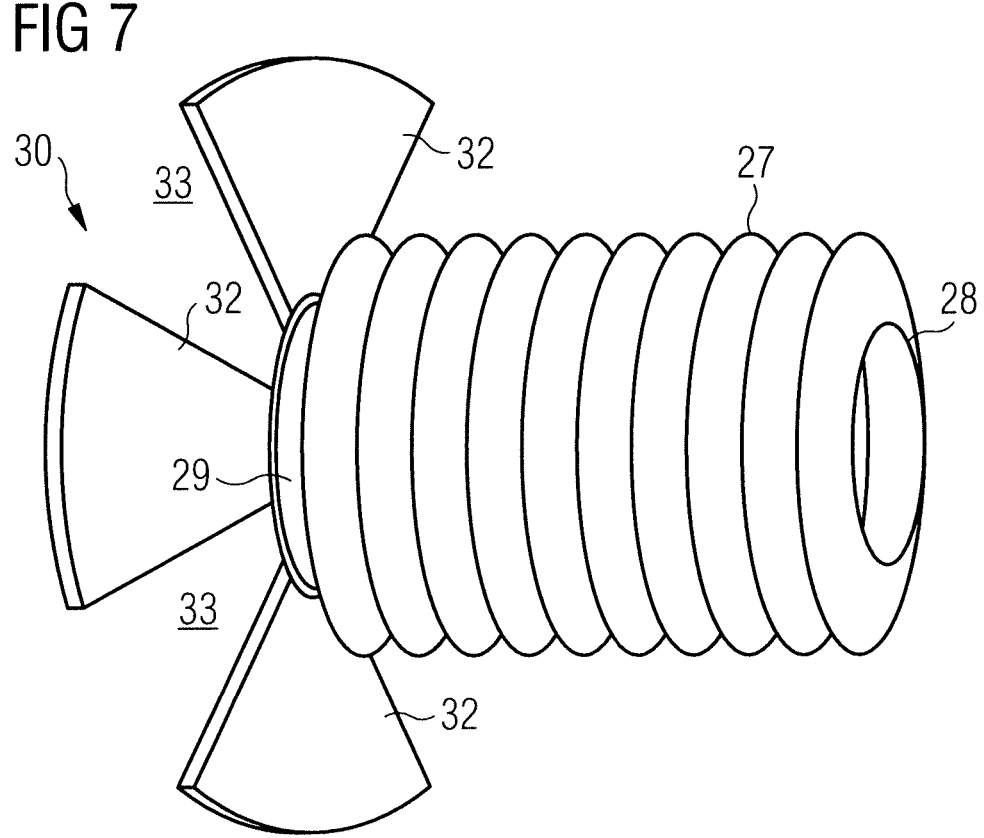
FIG. 7 shows an intermediate portion according to another embodiment.

As shown in FIGS. 6 and 7 the attachment member 30 may be designed in accordance with different embodiments. Preferably, the attachment member is made of or comprises a material that allows suturing the attachment member to the patient's heart. A suitable material may be a felt or the like. The attachment member 30 may be a disc, sheet or the like as shown in FIG. 6 and may assume any appropriate shape, such as rounded, circular, rectangular, polygonal or the like. For instance, a surgeon may adapt the size and shape by cutting the edges of the attachment member 30.

Figure 8A:
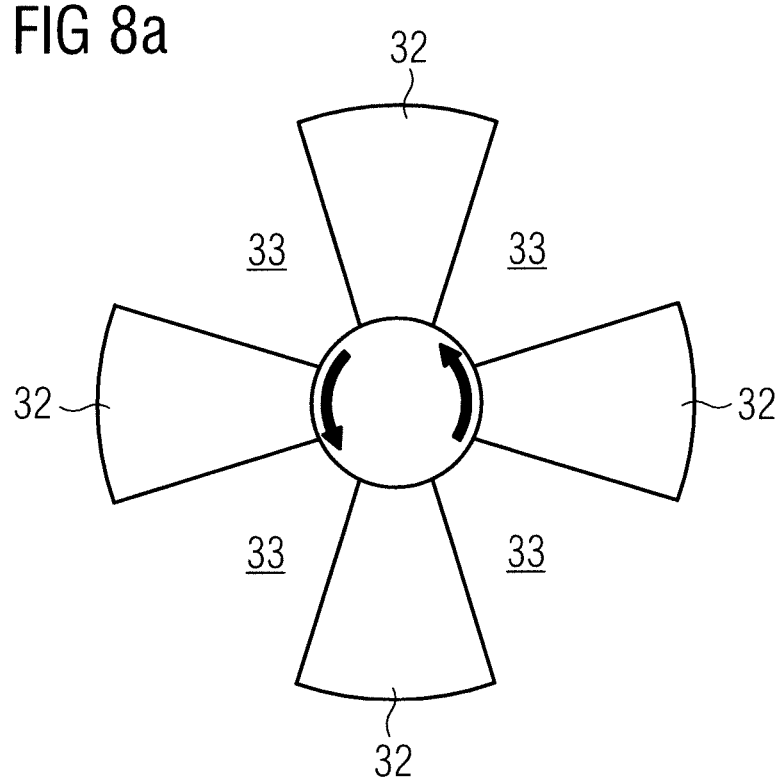
FIGS. 8a and 8b schematically show an attachment member during use.
Figure 8B:
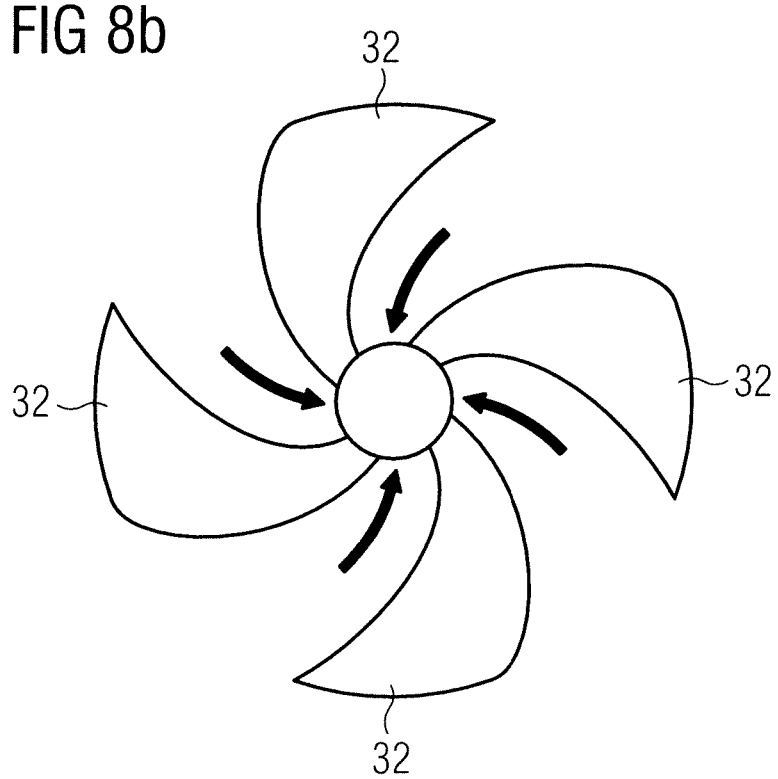

In another embodiment as shown in FIG. 7, the attachment member 30 may comprise a plurality of, such as three, four, five or six, sections 32 separated by respective gaps 33. The sections 32 extend radially from the intermediate portion 27. Referring again to FIGS. 5c to 5e and to FIGS. 8a and 8b, providing sections 32 instead of a continuous disc or sheet has the advantage that during twisting of the intermediate portion 27, the sections 32 get closer to each other and thereby twist and narrow the punch hole in the heart tissue as indicated by arrows in FIG. 8b, which reduces the wound size.

The invention claimed is:

1. A flow cannula for a blood pump for supporting a patient's heart, the flow cannula comprising:

a distal end of the flow cannula;
a proximal end of the flow cannula opposite the distal end of the flow cannula along a longitudinal axis of the flow cannula, the distal end of the flow cannula configured to be connected to a patient's heart or a blood vessel in order to establish a fluid communication between the blood pump and the patient's heart or between the blood pump and the blood vessel, respectively;
a distal portion of the flow cannula including the distal end of the flow cannula;
a proximal portion of the flow cannula including the proximal end of the flow cannula; and
an intermediate portion attached to either the distal portion of the flow cannula or the distal portion of the flow cannula and the proximal portion of the flow cannula, wherein the intermediate portion allows twisting thereof with a lower force than at least one of the distal portion of the flow cannula and the proximal portion of the flow cannula,
wherein the intermediate portion is configured to be fully occluded by twisting thereof when the intermediate portion is attached to the distal portion of the flow cannula and the proximal portion of the flow cannula, and
wherein at least a portion of the intermediate portion, alone or in combination with the distal portion of the flow cannula, is configured to be permanently attached to the patient's heart or the blood vessel.

2. The flow cannula of claim 1, wherein the intermediate portion has a distal end and a proximal end, the distal end of the intermediate portion being attached to the distal portion of the flow cannula and the proximal end of the intermediate portion being attached to the proximal portion of the flow cannula.

3. The flow cannula of claim 1, wherein the intermediate portion is attached to the distal portion of the flow cannula and the proximal portion of the flow cannula in a fluid tight manner in order to conduct a blood flow between the distal portion of the flow cannula and the proximal portion of the flow cannula.

4. The flow cannula of claim 1, wherein the intermediate portion is attached to the distal portion of the flow cannula and the proximal portion of the flow cannula such that the intermediate portion at least partially overlaps either the distal portion of the flow cannula or the distal portion of the flow cannula and the proximal portion of the flow cannula.

5. The flow cannula of claim 1, wherein the distal portion of the flow cannula and the proximal portion of the flow cannula are releasably connected to each other.

6. The flow cannula of claim 5, wherein the intermediate portion is axially gathered when the distal portion of the flow cannula and the proximal portion of the flow cannula are connected to each other.

7. The flow cannula of claim 1, wherein the intermediate portion comprises an attachment member at a distal end of the intermediate portion, the attachment member configured to be attached to the patient's heart, wherein a proximal end of the intermediate portion is attached to the proximal portion of the flow cannula.

8. The flow cannula of claim 1, wherein the intermediate portion is attached to the distal portion of the flow cannula and the proximal portion of the flow cannula such that the distal portion of the flow cannula and the proximal portion of the flow cannula are axially spaced from each other and the intermediate portion is disposed between the distal portion of the flow cannula and the proximal portion of the flow cannula.

9. The flow cannula of claim 1, wherein the intermediate portion is a flexible tubular member.

10. The flow cannula of claim 1, wherein the intermediate portion is stretchable in a direction of the longitudinal axis of the flow cannula.

11. The flow cannula of claim 1, wherein the intermediate portion has a wall thickness of about 5 µm to about 1,000 µm.

12. The flow cannula of claim 1, wherein the intermediate portion comprises a tubular polymer film configured to induce tissue ingrowth into the tubular polymer film.

13. A blood pump for supporting a patient's heart, the blood pump comprising:
   a pump casing including at least a first inlet and a first outlet;
   an impeller disposed in the pump casing, the impeller configured to draw blood into the pump casing;
   an outflow cannula having a proximal end and a distal end, the proximal end of the outflow cannula coupled to the pump casing at the first outlet, the distal end of the outflow cannula configured to be attached to a patient's aorta; and
   an inflow cannula coupled to the pump casing at the first inlet, the inflow cannula comprising:
   a distal end of the inflow cannula;
   a proximal end of the inflow cannula opposite the distal end of the inflow cannula along a longitudinal axis of the inflow cannula, the distal end of the inflow cannula configured to be connected to a patient's heart or a blood vessel in order to establish a fluid communication between the blood pump or between the blood pump and the patient's heart and the blood vessel, respectively;
   a distal portion of the inflow cannula including the distal end of the inflow cannula;
   a proximal portion of the inflow cannula including the proximal end of the inflow cannula; and
   an intermediate portion attached to either the distal portion of the inflow cannula or the distal portion of the inflow cannula and the proximal portion of the inflow cannula, wherein the intermediate portion allows twisting thereof with a lower force than at least one of the distal portion of the inflow cannula and the proximal portion of the inflow cannula,
   wherein the intermediate portion is configured to be fully occluded by twisting thereof when the intermediate portion is attached to the distal portion of the inflow cannula and the proximal portion of the inflow cannula, and
   wherein at least a portion of the intermediate portion, alone or in combination with the distal portion of the inflow cannula, is configured to be permanently attached to the patient's heart or the blood vessel.

14. The blood pump of claim 13, wherein the blood pump is sized and configured to be placed in a thoracic cavity of the patient.

15. The flow cannula of claim 4, wherein the intermediate portion at least partially overlaps each of the distal portion of the flow cannula and the proximal portion of the flow cannula.

16. The flow cannula of claim 7, wherein the distal portion of the flow cannula and the proximal portion of the flow cannula are integrally formed.

17. The flow cannula of claim 11, wherein the intermediate portion has a wall thickness of less than about 150 µm.

18. The flow cannula of claim 11, wherein the intermediate portion has a wall thickness of less than about 50 µm.

19. The flow cannula of claim 11, wherein the intermediate portion has a wall thickness of about 30 µm.

20. The flow cannula of claim 12, wherein the tubular polymer film comprises polyethylene terephthalate.

21. The flow cannula of claim 1, wherein the intermediate portion comprises a polymer tube configured to induce tissue ingrowth into the polymer tube.

22. The flow cannula of claim 21, the polymer tube comprising one of silicone or polyurethane.

23. A system comprising:
   a flow cannula, wherein the flow cannula is the flow cannula of claim 18; and
   a blood pump, the blood pump comprising:
   a pump casing including at least a first inlet and a first outlet;
   an impeller disposed in the pump casing, the impeller configured to draw blood into the pump casing; and
   an outflow cannula having a proximal end and a distal end, the proximal end of the outflow cannula coupled to the pump casing at the first outlet, the distal end of the outflow cannula configured to be attached to a patient's aorta,
   wherein the pump casing is coupled to the flow cannula at the first inlet.

24. A flow cannula for a blood pump for supporting a patient's heart, the flow cannula comprising:
   a distal end of the flow cannula;
   a proximal end of the flow cannula opposite the distal end of the flow cannula along a longitudinal axis of the flow cannula, the distal end of the flow cannula configured to be connected to a patient's heart or a blood vessel in order to establish a fluid communication between the blood pump and the patient's heart or between the blood pump and the blood vessel, respectively;
   a distal portion of the flow cannula including the distal end of the flow cannula;
   a proximal portion of the flow cannula including the proximal end of the flow cannula; and
   an intermediate portion attached to either the distal portion of the flow cannula or the distal portion of the flow cannula and the proximal portion of the flow cannula, wherein the intermediate portion allows twisting thereof with a lower force than at least one of the distal portion of the flow cannula and the proximal portion of the flow cannula,
   wherein the intermediate portion is configured to be fully occluded by twisting thereof,
   wherein at least a portion of the intermediate portion is configured to be permanently attached to the patient's heart or the blood vessel, and
   wherein the proximal portion of the flow cannula and distal portion of the flow cannula are formed as a single piece.

* * * * *

UNITED STATES PATENT AND TRADEMARK OFFICE
CERTIFICATE OF CORRECTION

PATENT NO. : 11,235,140 B2
APPLICATION NO. : 16/329252
DATED : February 1, 2022
INVENTOR(S) : Thorsten Siess et al.

It is certified that error appears in the above-identified patent and that said Letters Patent is hereby corrected as shown below:

In the Specification

Column 7, Line 29:
Now reads: "5, 6."; should read – 6, 5. –

Column 7, Line 29:
Now reads: "5, 6"; should read – 6, 5 –

Column 8, Line 9:
Now reads: "5, 6"; should read – 6, 5 –

Column 8, Line 27:
Now reads: "15"; should read – 16 –

Column 8, Line 28:
Now reads: "16"; should read – 15 –

Column 8, Line 43:
Now reads: "intermediated"; should read – intermediate –

Column 8, Line 62:
Now reads: "forming."; should read – formed. –

Signed and Sealed this
Ninth Day of August, 2022

Katherine Kelly Vidal
*Director of the United States Patent and Trademark Office*